United States Patent
Zarling et al.

(10) Patent No.: US 9,498,352 B2
(45) Date of Patent: Nov. 22, 2016

(54) METHOD FOR PRODUCING AN ARTIFICIAL FOOT

(75) Inventors: Sven Zarling, Duderstadt (DE); Martin Karstens, Göttingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 546 days.

(21) Appl. No.: 13/131,953

(22) PCT Filed: Dec. 1, 2009

(86) PCT No.: PCT/DE2009/001703
§ 371 (c)(1),
(2), (4) Date: May 31, 2011

(87) PCT Pub. No.: WO2010/063274
PCT Pub. Date: Jun. 10, 2010

(65) Prior Publication Data
US 2011/0230976 A1    Sep. 22, 2011

(30) Foreign Application Priority Data

Dec. 2, 2008 (DE) ..................... 10 2008 060 177

(51) Int. Cl.
*A61F 2/66* (2006.01)
*A61F 2/50* (2006.01)
*A61F 2/76* (2006.01)

(52) U.S. Cl.
CPC .............. *A61F 2/5046* (2013.01); *A61F 2/66* (2013.01); *A61F 2/76* (2013.01);
(Continued)

(58) Field of Classification Search
CPC . A61F 2/66; A61F 2002/6614; A61F 2/5046

USPC .......................................................... 623/53
See application file for complete search history.

(56) References Cited

U.S. PATENT DOCUMENTS 4,721,510 A * 1/1988 Cooper et al. .................. 623/55
5,482,513 A * 1/1996 Wilson ............................ 623/52
(Continued)

FOREIGN PATENT DOCUMENTS

CN    2776340 Y    5/2006
DE    29920434 U1    5/2000
(Continued)

OTHER PUBLICATIONS

Mosler, L., Mechanik and Biomechanik: Welche Auswirkungen haben Meβbare Eigenschafen von Prothesenfüβen (Mechanics and Biomechanics: What Effects do Measurable Properties of Prosthetic Feet Have?); Med. Orth. Tech., No. 4, vol. 122, pp. 114-117, 2002.

*Primary Examiner* — Bruce E Snow
*Assistant Examiner* — Melissa Hoban
(74) *Attorney, Agent, or Firm* — Holland & Hart

(57) ABSTRACT

The invention relates to a method for producing an artificial foot, comprising a medial plane (M) in a longitudinal axis, in which a nominal foot length (l) is defined as a distance from a heel to a foot tip of a natural foot replaced by the artificial foot, and designed having a top side connecting piece (4) for torsionally rigidly connecting a foot insert (2) extending substantially over the length of the foot (l), and contacting two contact surfaces (6, 7) over the length (l), of which a first heel side contact surface (7) is located in the heel area and a second ball side contact surface (6) is located in the ball area, and designed so that the connecting part (4) is connected to the contact surfaces (6, 7) of the foot part by means of spring connections.

16 Claims, 14 Drawing Sheets

(52) U.S. Cl.
CPC ............... *A61F 2002/5009* (2013.01); *A61F 2002/5079* (2013.01); *A61F 2002/665* (2013.01); *A61F 2002/6614* (2013.01); *A61F 2002/6664* (2013.01); *A61F 2002/6671* (2013.01); *A61F 2002/6685* (2013.01); *Y10T 29/49* (2015.01)

(56) References Cited

U.S. PATENT DOCUMENTS

| | | | | |
|---|---|---|---|---|
| 5,509,938 | A | * | 4/1996 | Phillips ............... 623/56 |
| 5,695,526 | A | * | 12/1997 | Wilson ............... 623/49 |
| 5,800,570 | A | * | 9/1998 | Collier ............... 623/55 |
| 7,364,593 | B2 | * | 4/2008 | Townsend et al. ............... 623/52 |
| 2003/0074085 | A1 | * | 4/2003 | Slemker et al. ............... 623/35 |
| 2003/0144745 | A1 | | 7/2003 | Phillips |
| 2008/0140221 | A1 | * | 6/2008 | Macomber et al. ............... 623/27 |
| 2008/0262635 | A1 | | 10/2008 | Moser et al. |
| 2008/0288086 | A1 | * | 11/2008 | Auberger et al. ............... 623/27 |

FOREIGN PATENT DOCUMENTS

| | | |
|---|---|---|
| DE | 102005008161 A1 | 8/2006 |
| DE | 102006004132 A1 | 8/2007 |
| GB | 2433443 A | 6/2007 |
| WO | 2005048887 A1 | 6/2005 |

* cited by examiner

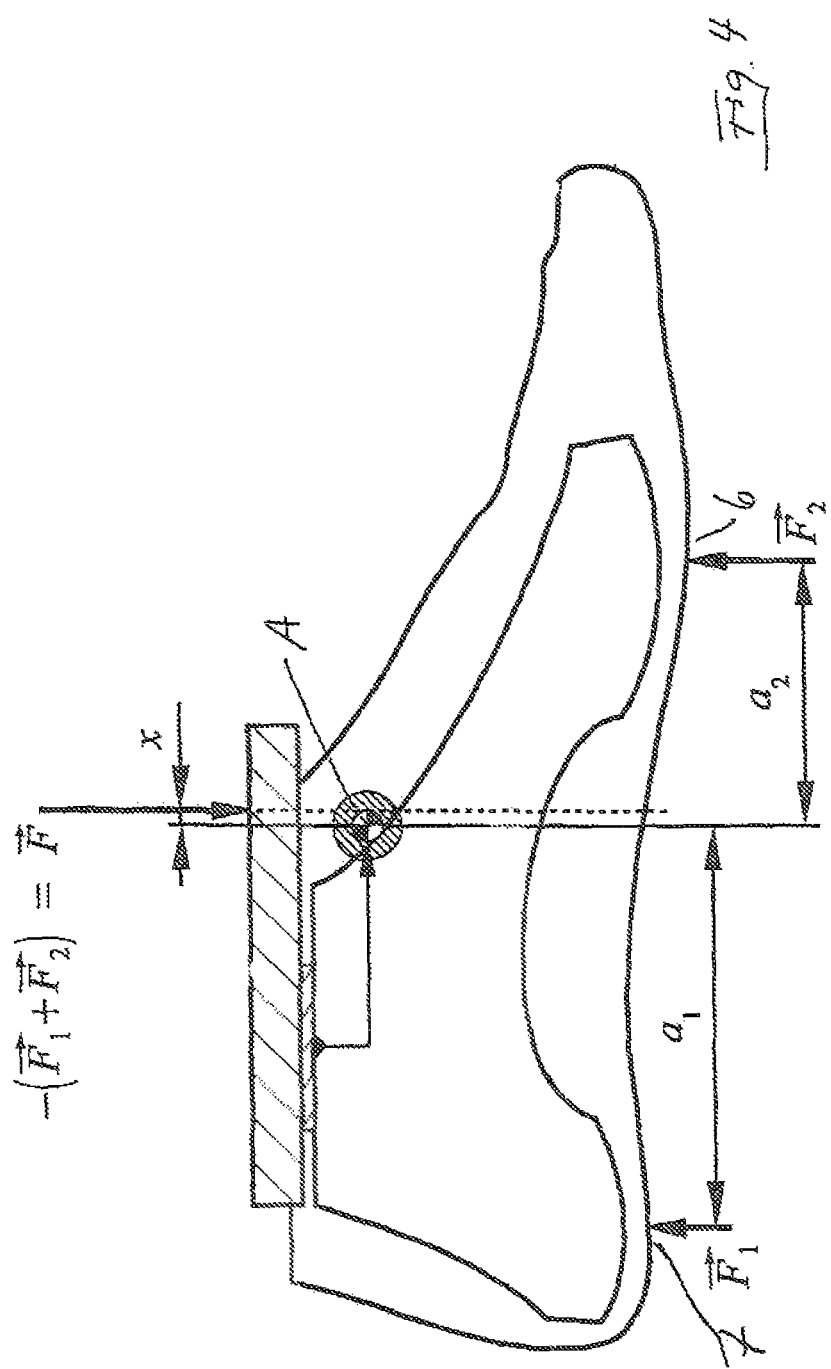

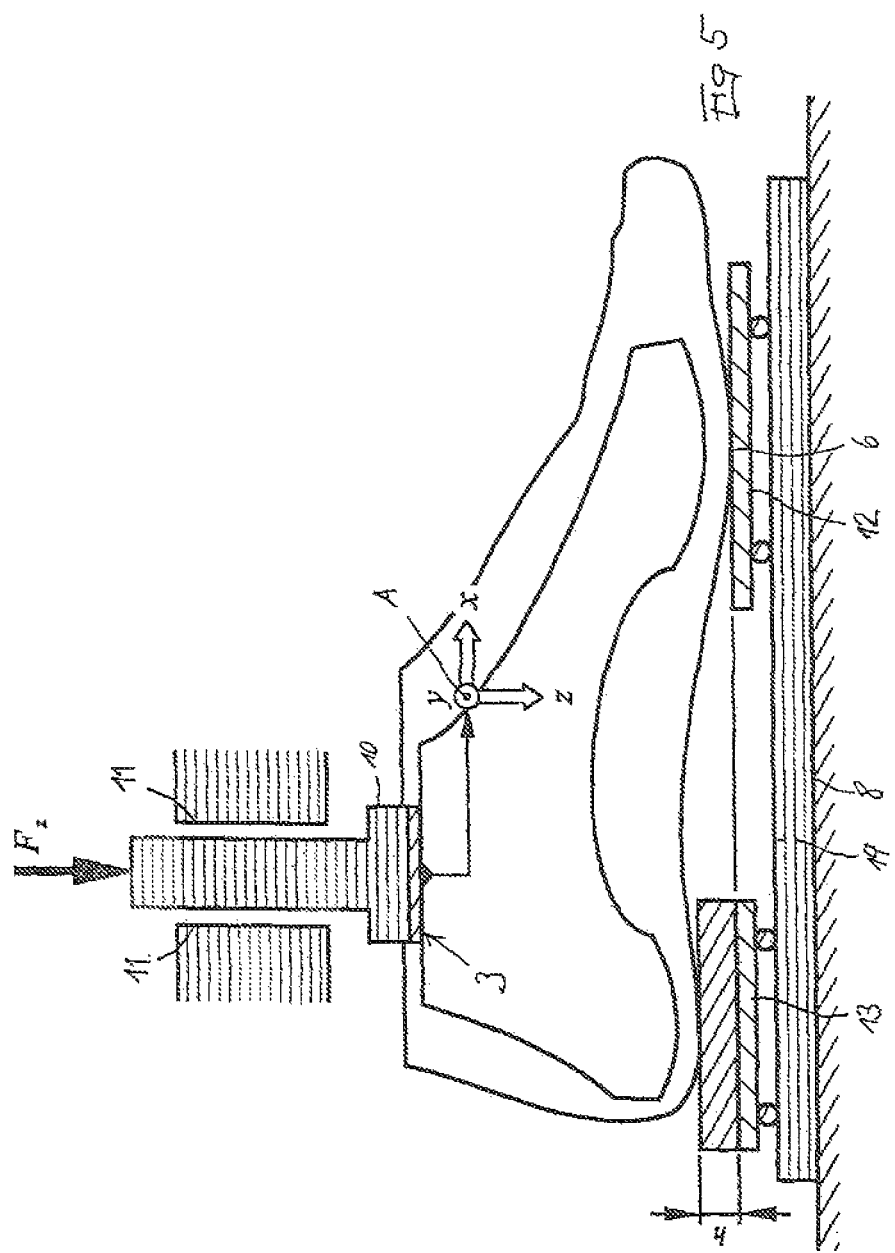

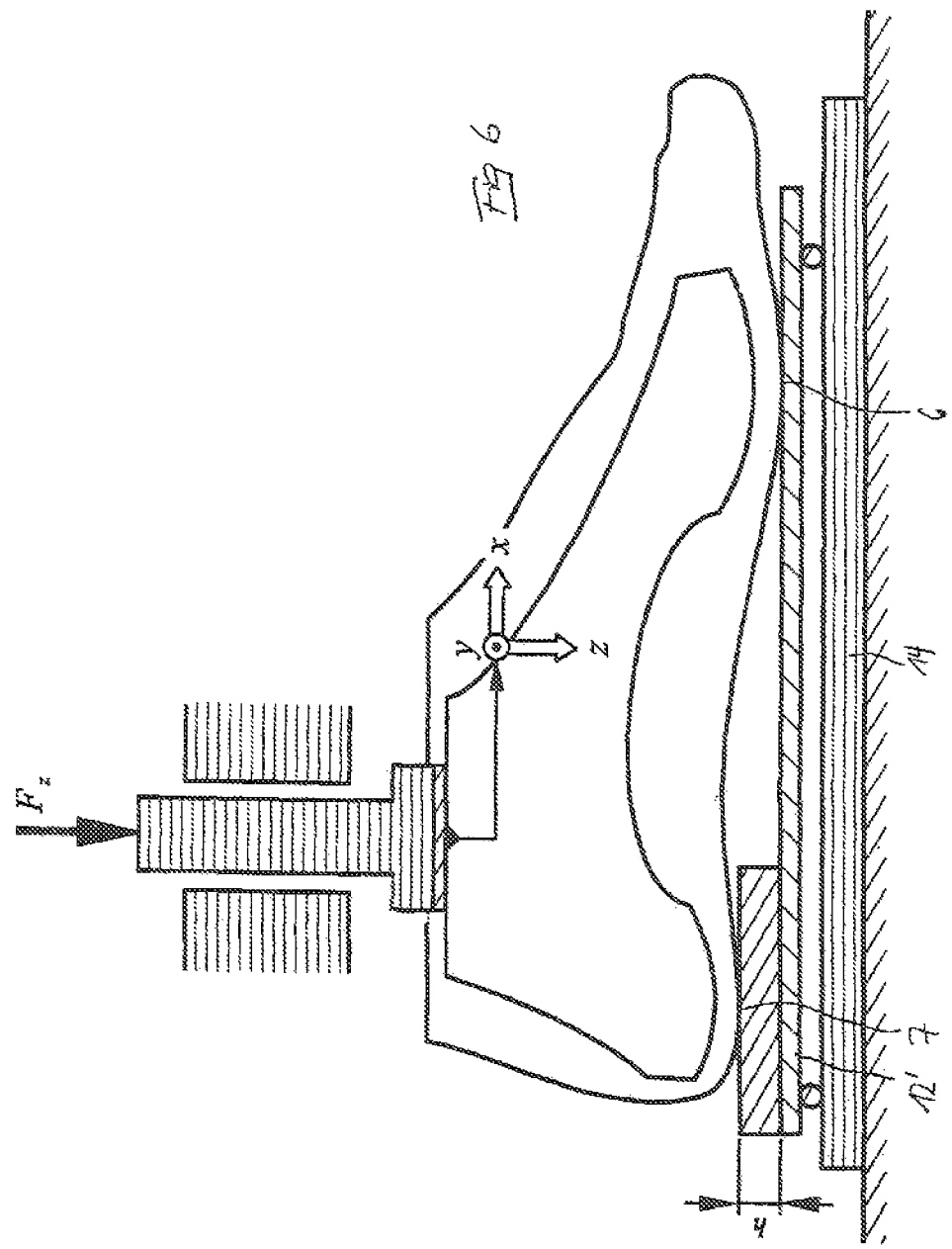

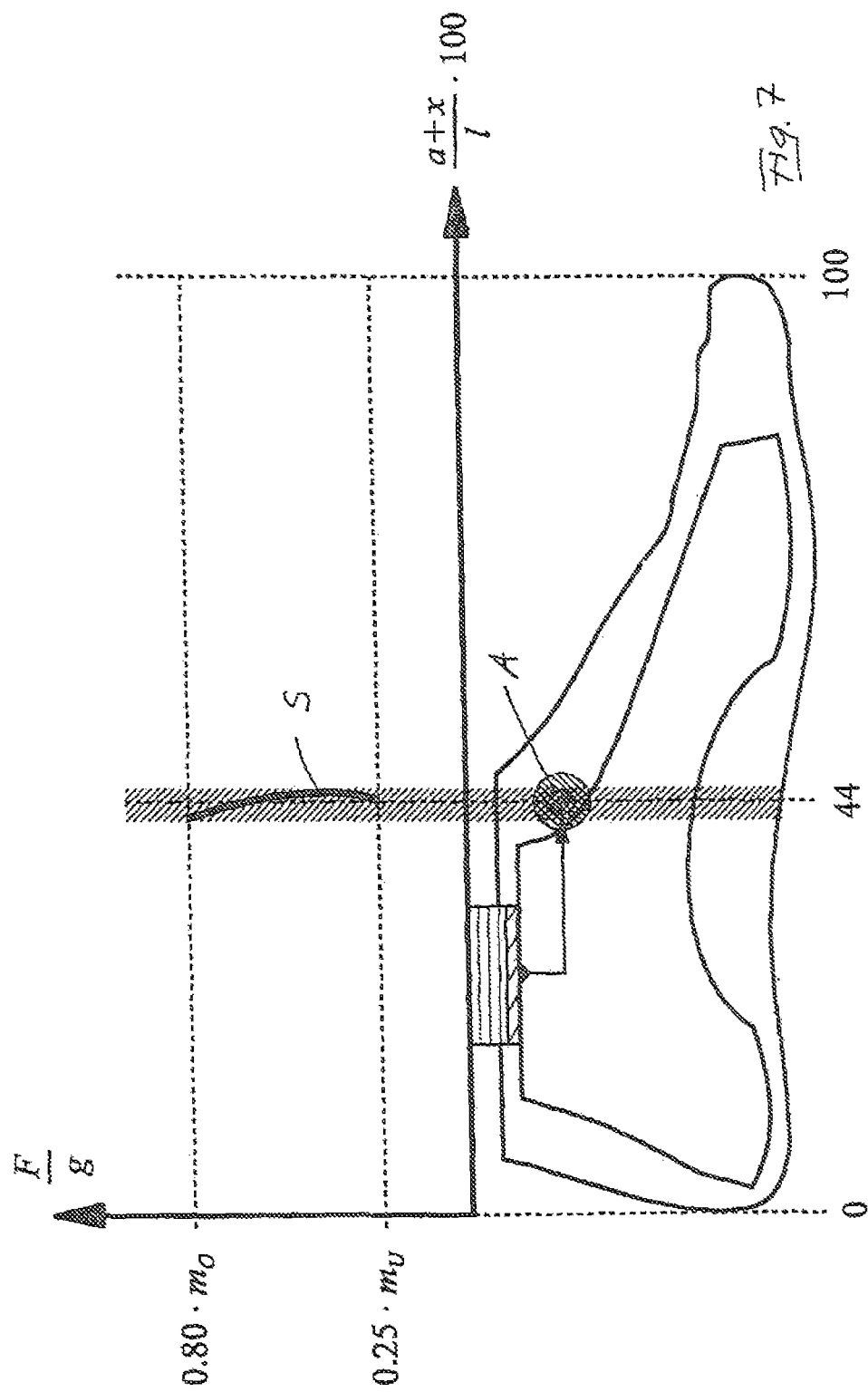

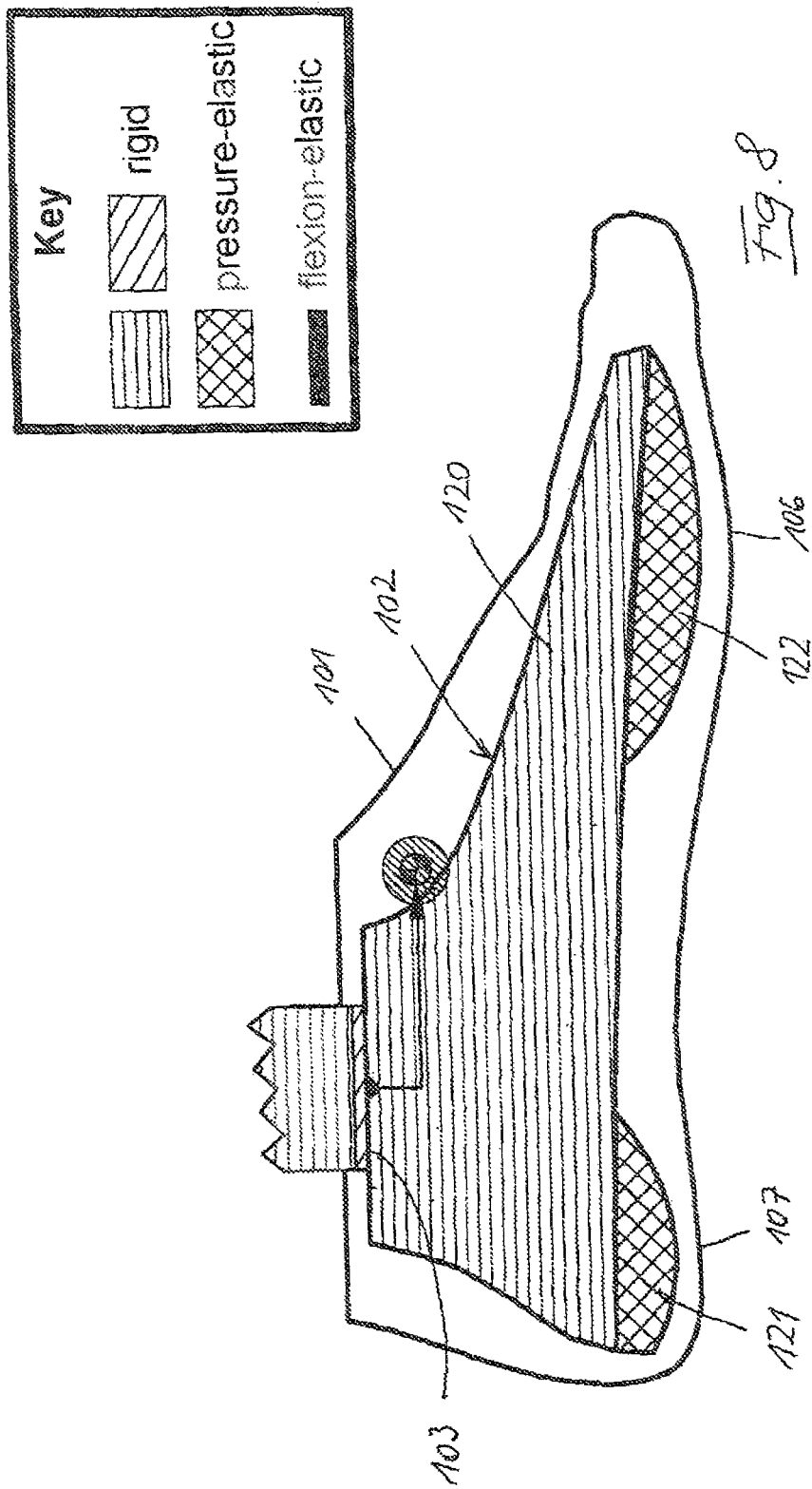

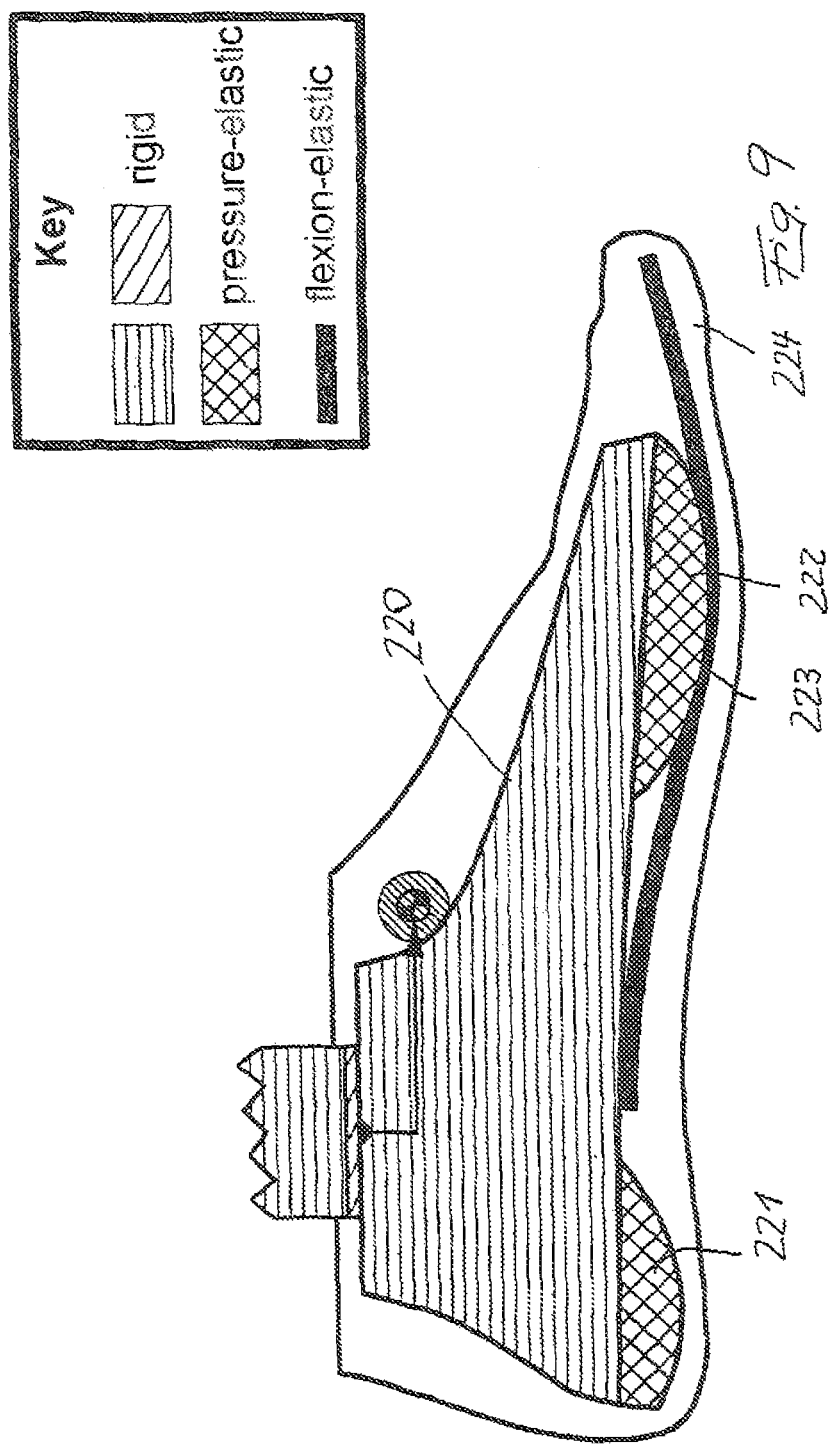

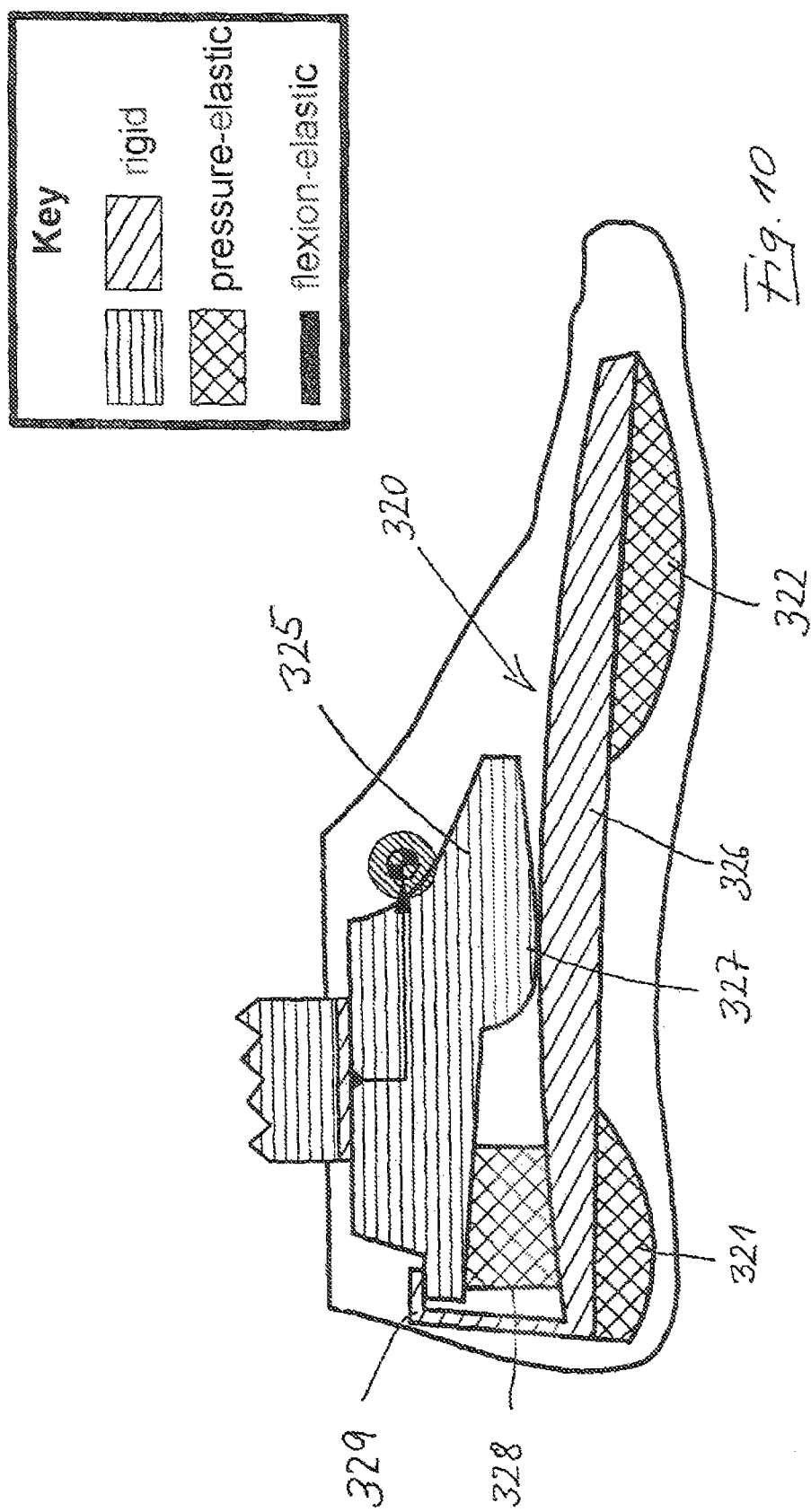

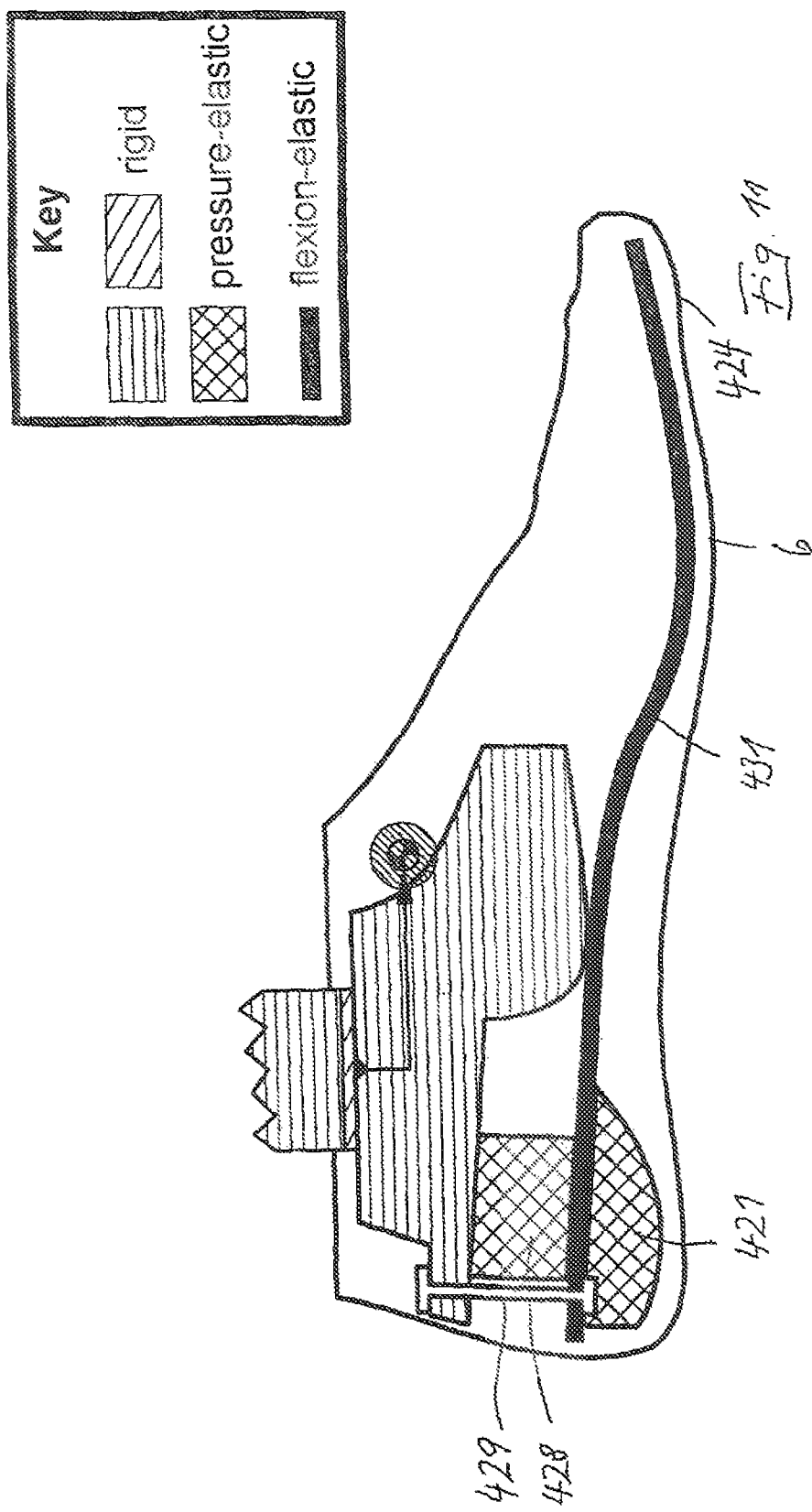

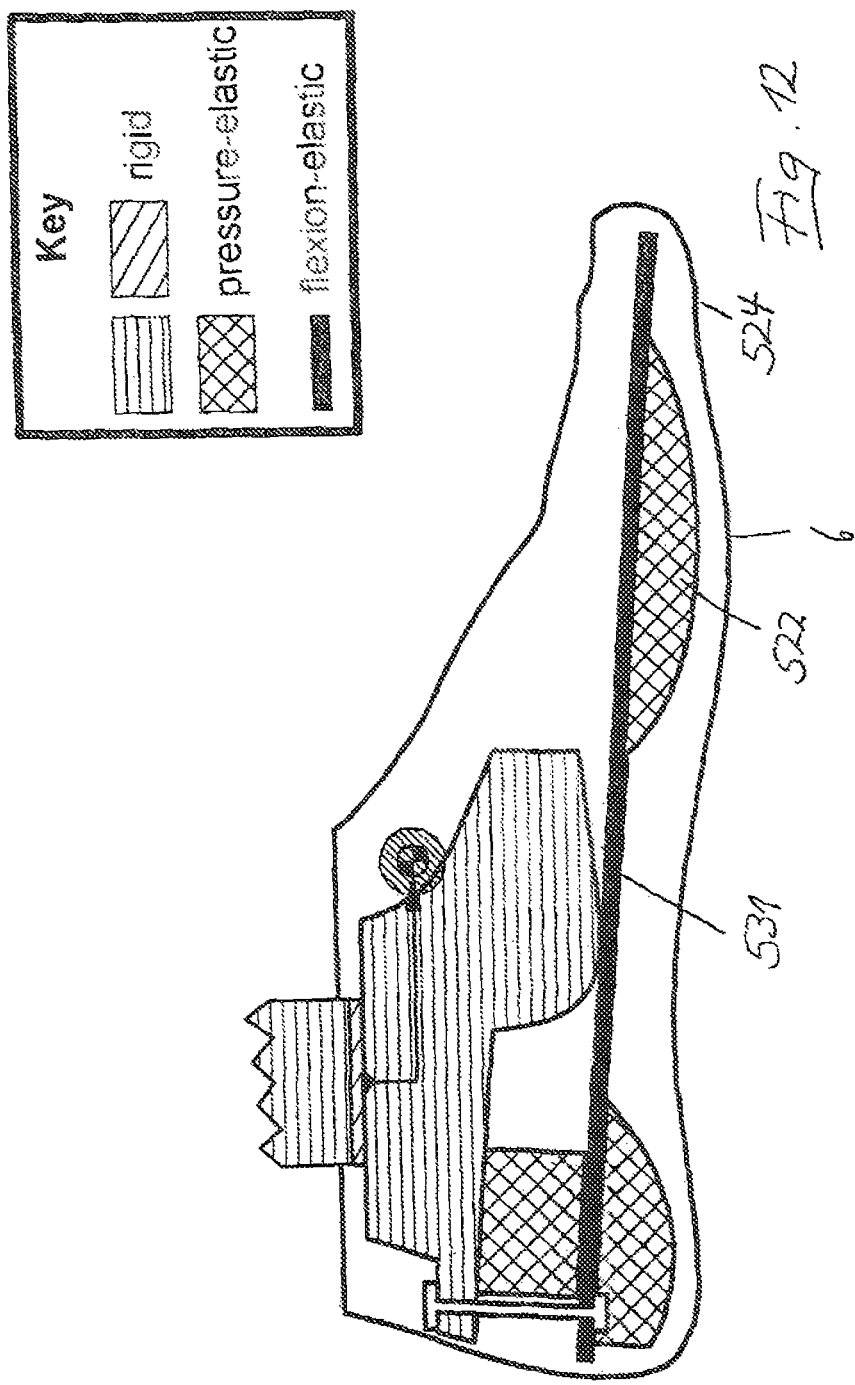

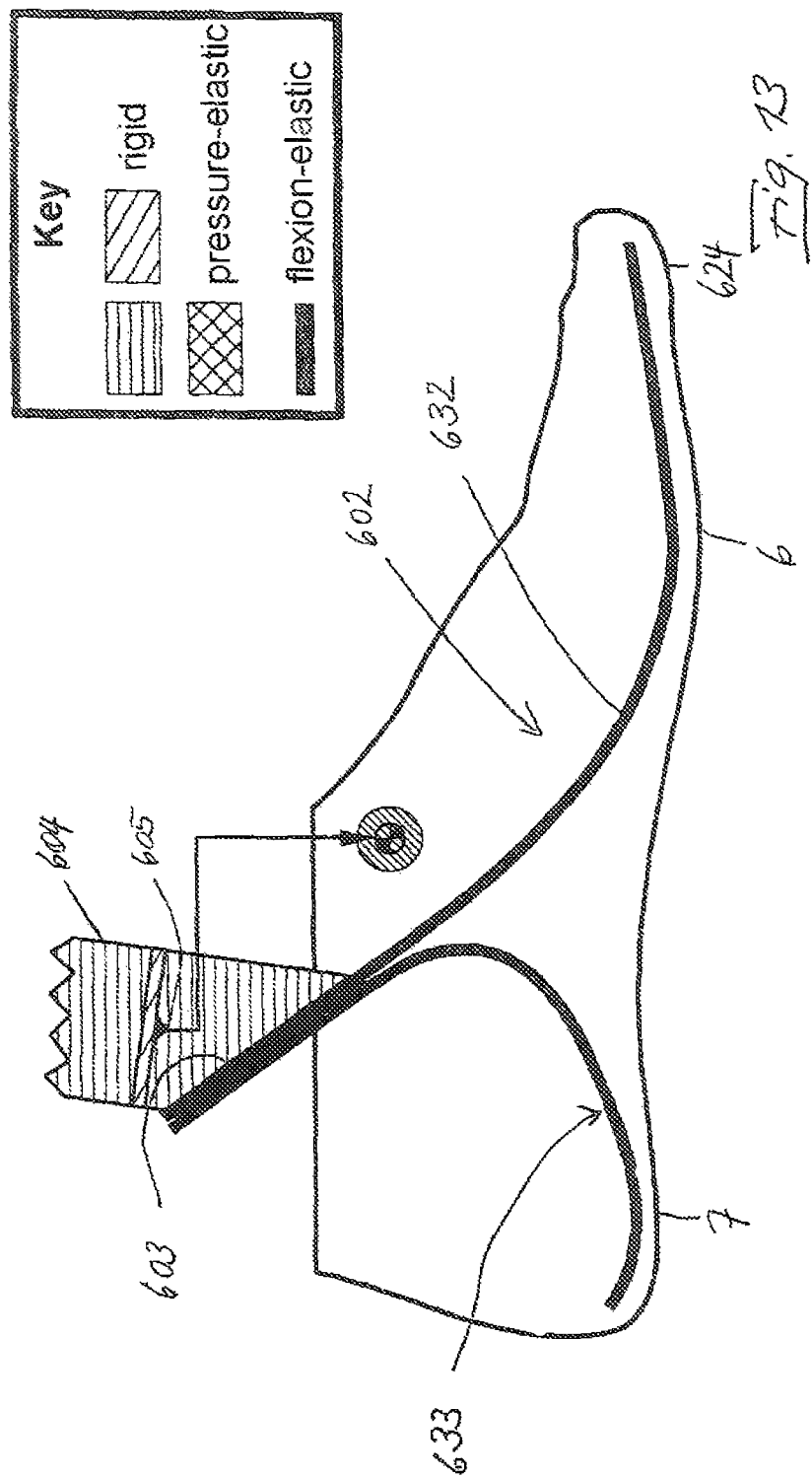

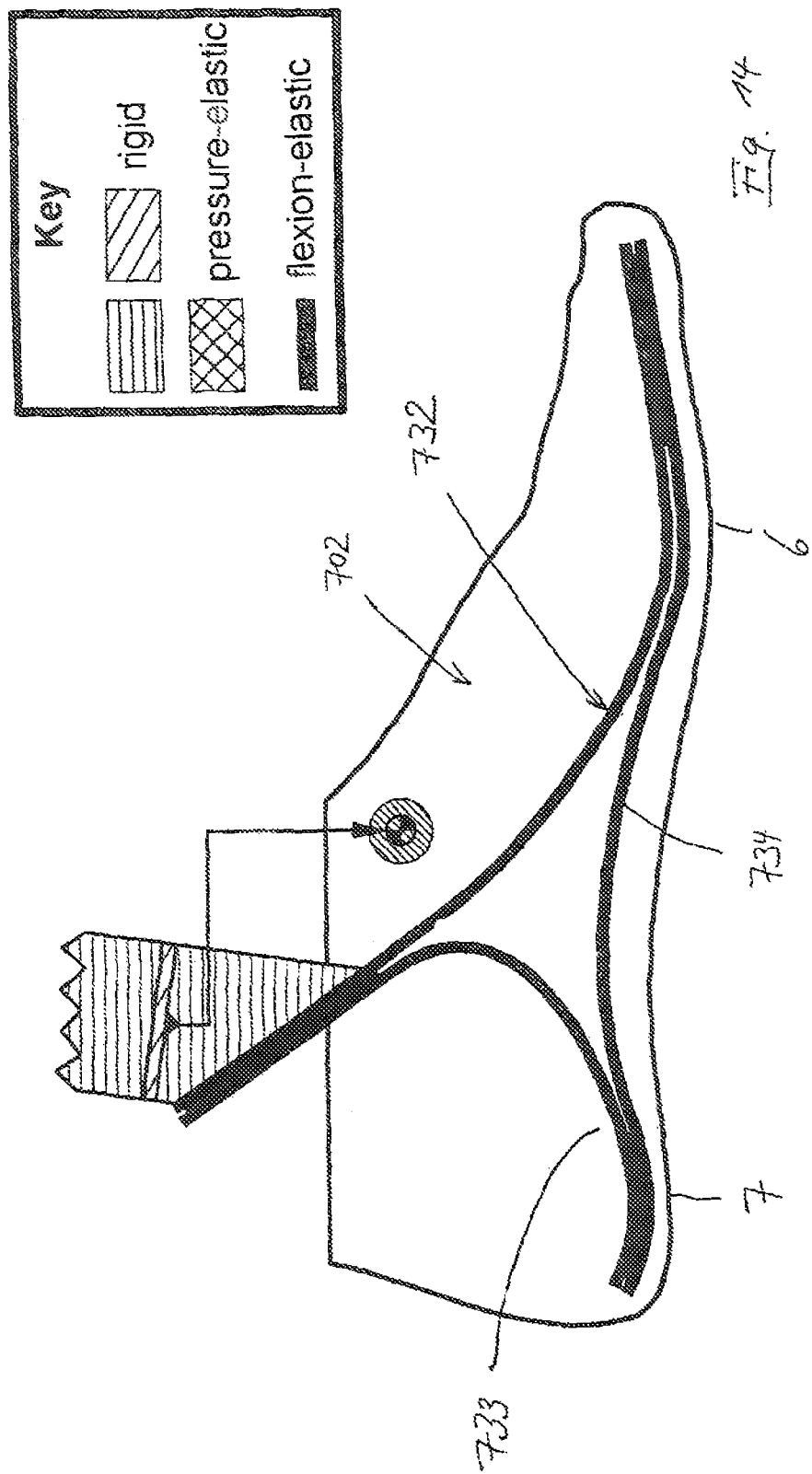

METHOD FOR PRODUCING AN ARTIFICIAL FOOT

TECHNICAL FIELD

The invention relates to a method for producing an artificial foot which, in a longitudinal direction, has a medial plane in which a nominal foot length is defined as a distance from a heel to a foot tip of a natural foot replaced by the artificial foot, and which is designed with a top connector piece for the torsionally rigid connection of a foot insert extending substantially along the length of the foot, and which, seen along the length, bears on two contact surfaces, of which a first heel-side contact surface is located in the heel area and a second ball-side contact surface is located in the ball area, and which is designed such that the connector part is connected to the contact surfaces of the foot part by spring connections.

BACKGROUND

Artificial feet of this kind are known in numerous designs. They have been optimized in many respects. An important function of an artificial foot is to ensure the most natural possible gait in the walking cycle, the aim being to give the prosthesis wearer a secure feeling when walking. In addition, the artificial foot is intended to permit a stance that is as stable as possible and that feels secure.

It has been found that artificial feet can be produced which are particularly suitable for the walking cycle but which do not give a secure feeling when standing on the artificial foot. By contrast, if the artificial foot is optimized for standing, the gait is adversely affected by an insecure feeling during walking.

SUMMARY

The object of the present invention is therefore to make available a method for producing an artificial foot, by which means a good gait and also a secure feeling when standing are imparted by the artificial foot.

The present invention proceeds from the recognition that, in a natural leg with a natural foot, the resulting force vector (body vector) formed by the ground reaction forces lies some distance in front of the ankle joint acting as the point of load introduction from the lower leg to the foot. It is therefore known in principle to provide a corresponding construction for artificial feet too, in other words to arrange the body vector resulting from a vectorial sum of ground reaction forces in front of a load introduction axis via which weight forces are introduced into the artificial foot. Since the load introduction into the artificial foot does not then take place in a line extending through the joint axis, a torque occurs across the horizontal distance lever in the joints at the change-over from the unloaded foot to the foot loaded by the weight.

According to the invention, in order to solve the above-mentioned problem, a method for producing an artificial foot of the type mentioned at the outset is characterized by a) designing the curved contact surfaces to an approximately linear contact surface on a support, b) positioning a body vector as resulting force vector of the ground reaction forces occurring on the contact surfaces in the rest state in a range between 40% and 48% of the nominal foot length, measured from the heel, c) loading the foot with weight loads between 25% of the minimal permissible and 80% of the maximum permissible body weight, and d) adapting the spring connections between the connector part and the contact surfaces in such a way that, during the loading according to method step d), the body vector shifts by less than ±4% of the nominal foot length.

The present invention is based on the concept that a secure feeling when the prosthesis wearer is standing presupposes that the resulting force vector (body vector) from the ground reaction forces occurring on the contact surfaces should not substantially change its position in the longitudinal direction when the load on the artificial foot varies. Such a change in the body vector takes place in the known set-ups of artificial feet. According to the invention, the spring connections between the connector part and the contact surfaces of the foot part are adapted to each other in such a way that, when the load on the artificial foot varies, the body vector does not substantially shift in the longitudinal direction, i.e. does not exceed a variation of ±4%, preferably of ±2%. It is also important in the present invention that the body vector is located within a predetermined range, namely between 40 and 48% of the nominal foot length, measured from the heel, the optimal setting being 44%, if appropriate ±1%.

Designing the curved contact surfaces to an approximately linear contact surface on a support has the purpose of ensuring defined contact surfaces which, when the weight shifts in the sagittal plane, do not lead to a change, or lead only to a very slight change, in the position of the contact surface in the longitudinal direction (in the sagittal plane). The linear contact surface can therefore also be formed by punctiform contact surfaces that form a resulting line.

It has been shown that an artificial foot produced according to the invention provides a secure feel when standing, corresponding to the feel when standing on a healthy foot. In addition, the artificial foot produced according to the invention can be readily designed to give a natural and secure feel when the prosthesis wearer is walking.

It is preferable overall if the body vector resulting from the ground reaction forces remains between 42 and 46% of the nominal foot length.

A resting state arises when the body is upright and the body load is distributed uniformly on both feet, such that the musculature is stressed only slightly. Measurements of the line of gravity in the resting state have shown that the body vector, starting from the center of the head (auditory canal), runs 1 cm anterior of the vertebral body L4 to a point 1.5 to 5 cm in front of the upper part of the ankle joint. The resting state is not completely stable since slight compensating movements occur, which take place approximately 4 to 6 times per second with variations of up to 5 mm in the lateral direction and of up to approximately 8 mm in the anterior and posterior directions.

The artificial foot produced according to the invention can be made in several designs.

In a first embodiment, the foot insert can have a core and can be connected to the contact surfaces via elastic pieces. The core can in this case be inelastic, although it can also have a predetermined elasticity, which in particular decreases along the length of the foot part in the direction of the toe area.

The elastic pieces can be made of elastically compressible material and form the curved contact surfaces. Alternatively, it is possible to insert springs as elastic pieces between the contact surfaces and the core.

In a development of this embodiment, the connector part can be connected to the core via a joint which, upon loading starting from the rest state, permits an elastically damped rotation of the connector part relative to the heel-side contact surface. This embodiment permits an extended plantar flexion of the foot. This plantar flexion is preferably limited by a flexible and preferably inelastic limiting means in the direction of expansion of the spring.

It is also possible for the foot insert to be designed, substantially or completely without a rigid core, as a spring combination that has a spring extending to the heel-side contact surface and a spring extending to the ball-side contact surface, wherein the springs are connected to each other on the connector part. In another embodiment of this design principle, the springs can be connected to each other at the ground side via a further spring, which extends along the length of the foot part.

The springs of the spring combination are preferably formed by leaf springs.

In all cases, it is essential to the present invention that the elasticities between the contact surfaces and the connector part are adapted to each other such that the constant position according to the invention of the center of gravity defined by the ground reaction forces is ensured within the specified range.

BRIEF DESCRIPTION OF THE DRAWINGS

The invention is explained in more detail below on the basis of illustrative embodiments depicted in the drawing, in which:

FIG. 4 shows a schematic view of the spring connections between the contact surfaces and the connector part of the foot;

FIG. 5 shows a schematic view of an experiment for simulating the stance under different weight loads;

FIG. 6 shows a schematic view of a slightly modified experiment according to FIG. 3;

FIG. 7 shows a view of a line of gravity of an artificial foot produced according to the invention;

FIG. 8 shows a schematic view of a possible design of an artificial foot produced according to the invention, in a first embodiment;

FIG. 9 shows a schematic view of a possible design of an artificial foot produced according to the invention, in a second embodiment;

FIG. 10 shows a schematic view of a possible design of an artificial foot produced according to the invention, in a third embodiment;

FIG. 11 shows a schematic view of a possible design of an artificial foot produced according to the invention, in a fourth embodiment;

FIG. 12 shows a schematic view of a possible design of an artificial foot produced according to the invention, in a fifth embodiment;

FIG. 13 shows a schematic view of a possible design of an artificial foot produced according to the invention, in a sixth embodiment;

FIG. 14 shows a schematic view of a possible design of an artificial foot produced according to the invention, in a seventh embodiment.

DETAILED DESCRIPTION

Figure 1:
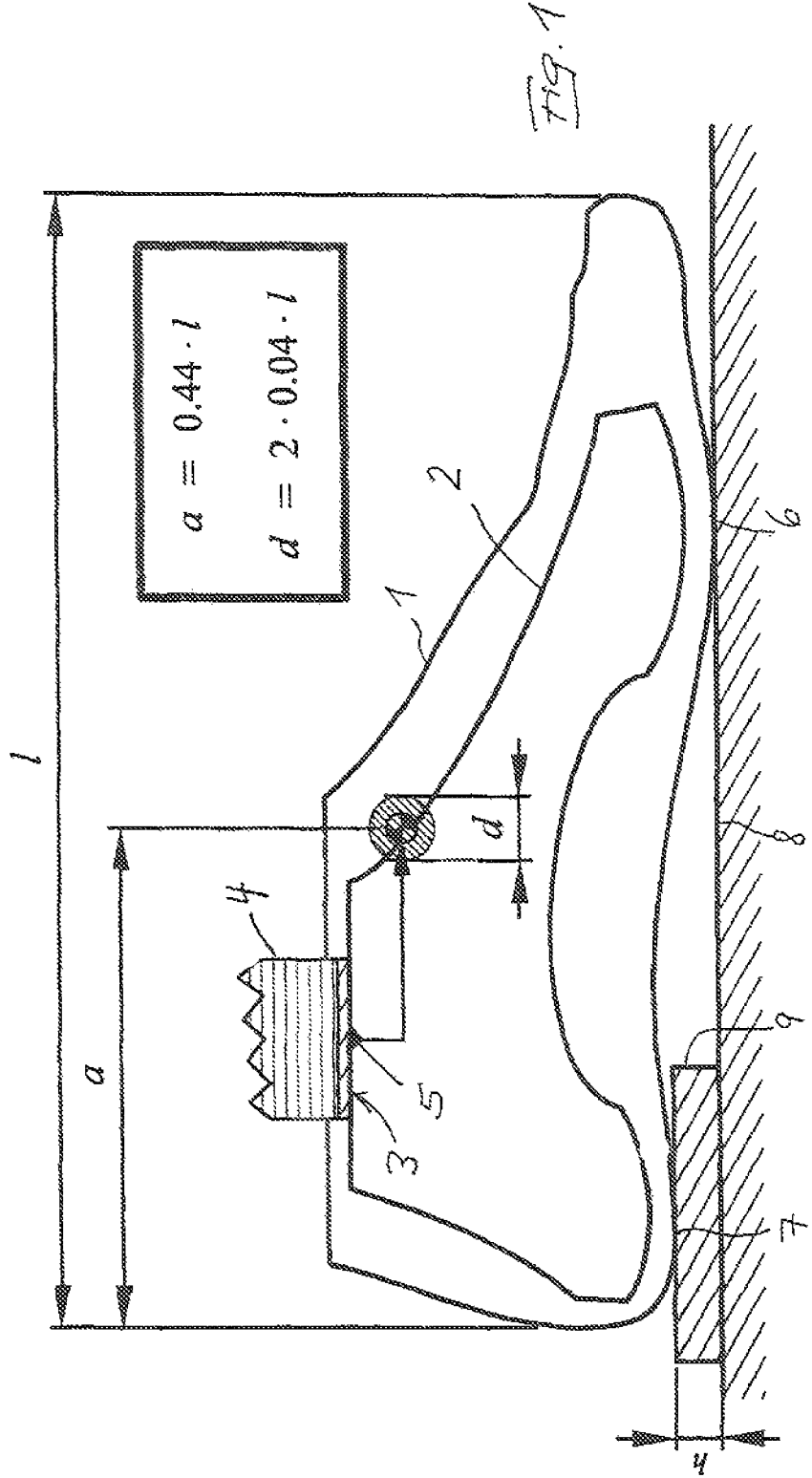
FIG. 1 shows a schematic side view of an artificial foot produced according to the invention.

FIG. 1 illustrates the basic set-up of an artificial foot which is formed by a cosmetic shell 1, imitating the shape and appearance of a natural foot, and by a foot insert 2. The foot part 2 has a connector 3 via which a lower leg prosthesis part 4 can be attached in a torsionally rigid manner to the artificial foot. Accordingly, the weight of the patient is introduced into the artificial foot via the connector 3. A force introduction point from the lower leg prosthesis part 4 into the artificial foot is indicated schematically.

The weight is distributed via the foot part 2 on two curved contact surfaces 6, 7, of which a ball-side contact surface 6 is designed approximately at the level of the ball of the foot, and a heel-side contact surface 7 is designed approximately at the level of the heel of the foot. The ball-side contact surface 6 is provided for placing on a support 8, while the heel-side contact surface 7 is designed to be placed on the support 8 via a standard heel height 9.

Figure 2:
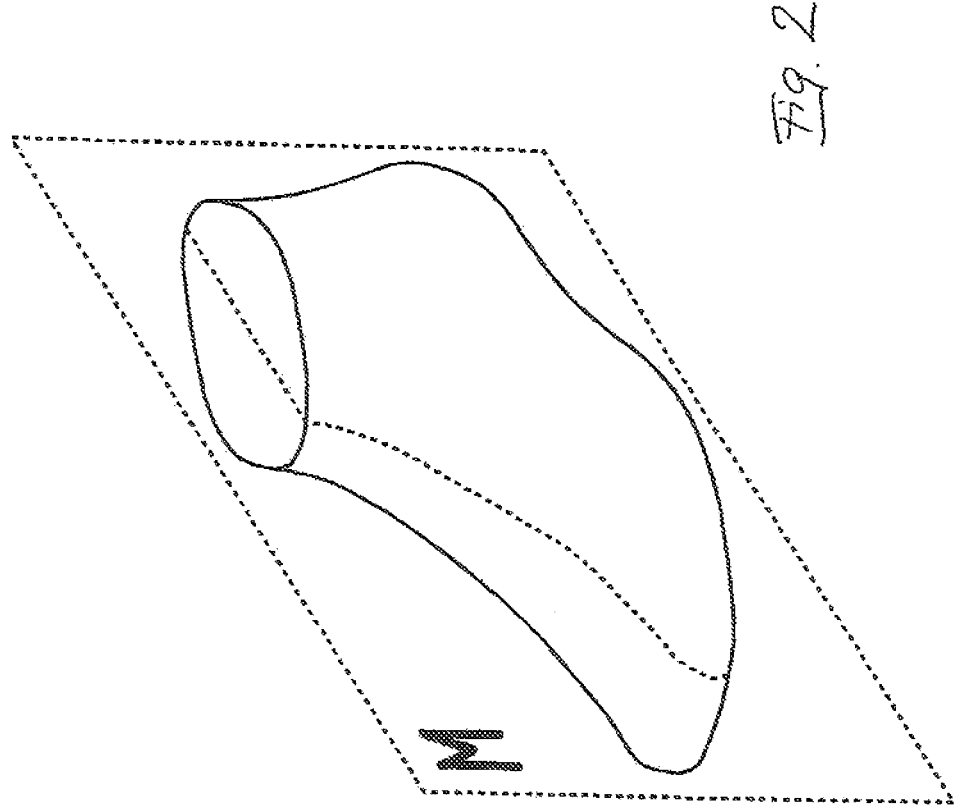
FIG. 2 shows a view of a sectional plane in the longitudinal center axis of the foot.

The artificial foot is constructed with a set-up reference point A through which the structural body vector of the prosthesis is intended to pass when the foot is not loaded. The artificial foot has a medial plane M, which is illustrated in FIG. 2. It lies vertically and contains the center axis in the longitudinal direction and the set-up reference point A.

The artificial foot has a nominal length l corresponding to the length of the natural foot that is to be replaced by the artificial foot.

The nominal length l runs in the medial plane M from the projection of the tip of the great toe to the projection of the heel.

In the foot according to the invention, the set-up reference point A lies at a distance of 0.44×l from the rear heel end. When the foot is loaded vertically, the force vector resulting from the ground reaction forces on the contact surfaces 6, 7 should be located within an area d, which has a radius of 0.04×l about the set-up reference point A, i.e. has a diameter of 2×0.04×l.

An artificial foot is designed for a weight range of a patient that ranges from a lower nominal weight mU to an upper nominal weight mO. The force vector resulting from the ground reaction forces on the contact surfaces 6, 7 should remain within the tolerance range d at a weight load of 0.25×mU to 0.8 mO.

Figure 3:
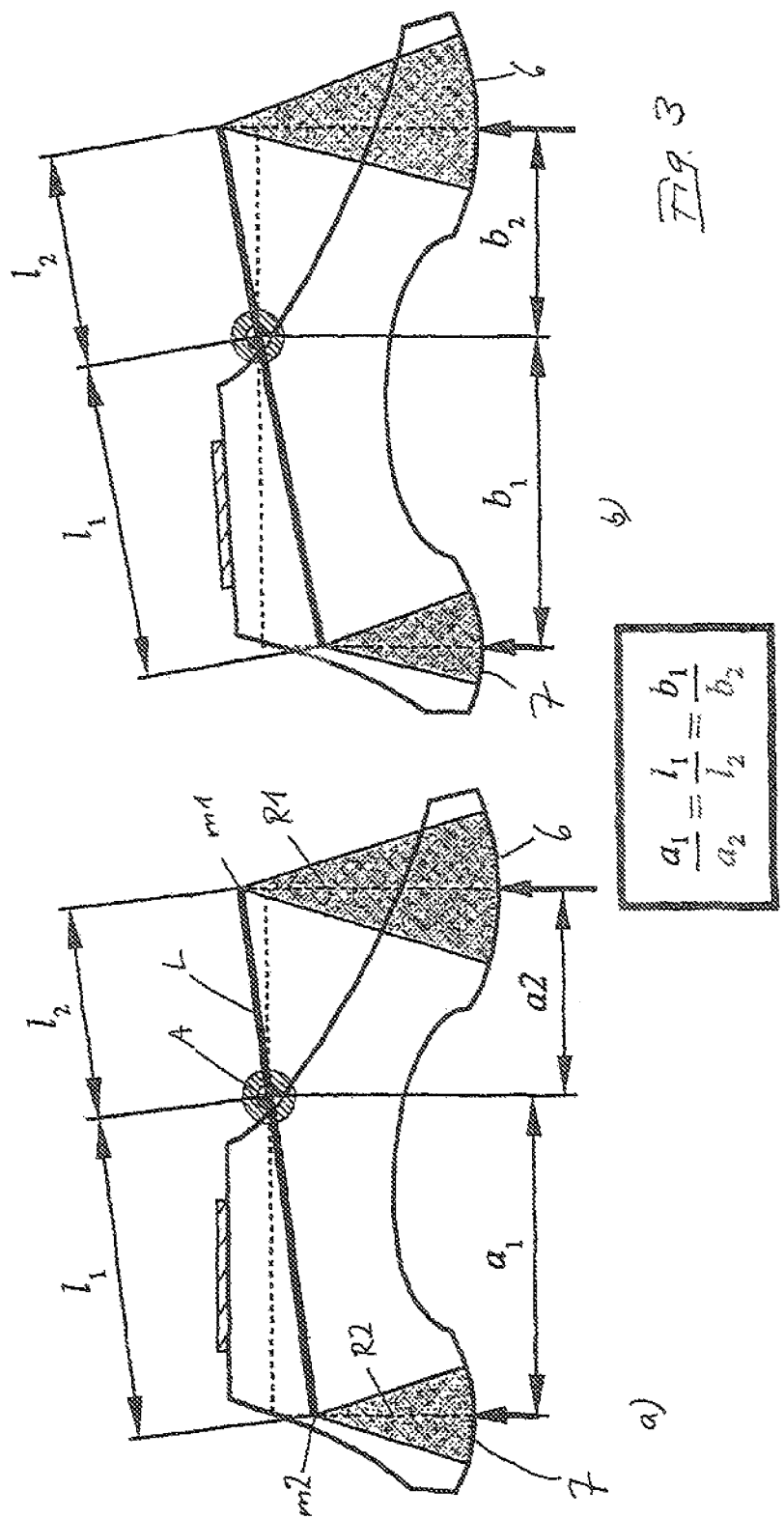
FIG. 3 shows a schematic view of the effect of different heel heights on the artificial foot produced according to the invention.

FIG. 3 illustrates the significance of the curved design of the contact surfaces 6, 7 and their function at changing heel heights.

FIG. 3a shows the artificial foot in its position with a nominal heel height. The curved contact surfaces 6, 7 are designed as arc sections in the medial plane M. The radii R1, R2 are chosen such that a connecting line L through the midpoints m1, m2 of the arcs of the contact surfaces 6, 7 extends through the set-up reference point A. In this design, the ratio of the distances a1, a2 from the contact lines 6, 7 to the projection of the set-up reference point A on the support 8 does not change, as can be discerned from FIG. 3b. In FIG. 3b, the artificial foot is shown without heel height. The contact lines of the contact surfaces 6, 7 thus shift, resulting in the distances b1 and b2. If the abovementioned condition for the curvature of the surfaces 6, 7 in the longitudinal direction is observed, this means that the ratios of the distances a1 to a2 and b1 to b2 are identical. The ratio corresponds to the unchanging distance of the midpoints m1 and m2 from the set-up reference point A along the connecting line L (11:12).

The effect of the foot according to the invention is based on adapting the spring connection between the contact lines of the contact surfaces 6, 7 and the set-up reference point A. This ratio thus remains the same, such that the adaptation of the spring paths for the nominal heel height (FIG. 3a) is also maintained for a changing heel height (FIG. 3b).

FIG. 4 illustrates the adjustment of the spring connections between the contact lines of the contact surfaces 6, 7 and the connector part 4 or the set-up reference point A. In the "simulated stance" explained in more detail below, the body vector runs through the tolerance area about the set-up reference point A. The adaptation of the spring connection is determined by the position of the two contact surfaces 6, 7 and by the force/travel characteristic curves of the two spring connections. For the adaptation, the following must apply:

$$a1 \times F1 \sim a2 \times F2.$$

This condition, just like the condition that the distance x of the body vector from the set-up reference point A should be <d/2, applies as follows for the changing load with $$0.25 \times mU < < 0.8 \ mO$$

This changing load is effected in the "simulated stance" mentioned below.

The compliance with the condition according to the invention is checked using a test for a simulated stance, as is shown in FIG. 5. For the test, the lower leg connector part 4 is replaced by a stamp 10 permitting a defined force introduction. The stamp is guided in a lateral guide 11 in such a way that it can perform movements only along a coordinate perpendicular to the support 8 and cannot perform rotation. Perpendicular to the coordinate z, the coordinates x and y span a plane parallel to the support 8. The zero point of the coordinates x and y is placed in the set-up reference point A. Sliding bearings 12, 13 are located under the contact surfaces 6, 7. In this way, the contact surfaces 6, 7 are freely movable along the x axis and are blocked along the y axis and the z axis. Underneath the sliding bearings 12, 13, there is a force measurement plate with which the force vector (body vector) resulting from the ground reaction forces on the contact surfaces 6, 7 can be determined by measurement technology.

Whereas separate sliding bearings 12, 13 are provided in the arrangement according to FIG. 5, a single sliding bearing 12' is provided in the modification according to FIG. 6. Therefore, in the modification, the deformation of the artificial foot under load gives rise to frictional forces along the x axis, as a result of which, however, the measured values are changed only slightly.

FIG. 7 illustrates that, for the weight load of 0.25%×mU to 0.8%×mO performed in the tests according to FIG. 5 or FIG. 6, the resulting force vector of the ground reaction forces lies within a range of variation that is smaller than the tolerance range d. According to the invention, the set-up reference point A, about which the position of the body vector according to the curve S varies, lies at 44% of the nominal length l of the artificial foot.

FIG. 8 shows a first illustrative embodiment of the design of an artificial foot according to the invention. The foot insert 102 is composed here of a rigid core 120, which forms the connector surface 103 and extends both into the ball area and also into the heel area of the artificial foot. In the heel area, a pressure-elastic and curved heel cushion 121 is attached to the core and determines the heel-side contact surface 107. The curvature of the contact surface 107 can be realized by the curved design both of the contact surface 7 and also of the foot part 102 lying behind it. The function of the curvature of the contact surface 107 is that a substantially linear contact face with the support 8 is produced, the position of which contact face does not substantially migrate when the artificial foot changes from a substantially unloaded state to a loaded state. This is clearly also possible by virtue of the fact that the heel cushion 121 has a curved design, since it comes into contact with the support 8 or the standard heel height 9 only via the cosmetic shell 101.

In a similar way in this illustrative embodiment, the curvature of the ball-side contact surface 106 is also determined by the fact that a pressure-elastic ball, cushion 122 is attached to the underside of the core 120. The elasticities of the heel cushion 121 and of the ball cushion 122 are adapted to each other in such a way as to meet the condition according to the invention whereby, upon loading of the artificial foot at between 0.25×mU and 0.8×mO, the resulting force vector of the ground reaction forces is intended to lie within the tolerance area d.

In the second embodiment of a foot according to the invention as shown in FIG. 9, the design features of the first embodiment have been carried over. In addition, a flexion-elastic spring 223 has been attached to the underside of the core 220 and, at a short distance from the heel cushion 221, extends along the underside of the ball cushion 222 and into a toe area 224 of the artificial foot. The flexion-elastic spring 223 is preferably designed as a leaf spring. In addition, upon roll-over at the end of the stance phase of the walking cycle, improved toe rigidity is achieved in conjunction with an enhanced feeling of safety.

The third embodiment of a foot according to the invention as shown in FIG. 10 is provided, as in the first embodiment shown in FIG. 6, with a heel cushion 321 and a ball cushion 322. In contrast to the first embodiment, the core 320 is composed of two rigid core parts, namely an upper core part 325 and a lower core part 326. The heel cushion 321 and the ball cushion 322 are located on the underside of the lower core part 326 extending along the length of the artificial foot, while the upper core part bears with a curved joint surface 327 on the top of the lower core part 326 and is coupled thereto, such that between the upper core part 325 and the lower core part 326 there is a joint connection that permits a pivoting of the upper core part 325 relative to the lower core part 326. In the heel area of the foot, a pressure-elastic cushion 328 is arranged between the underside of the upper core part 325 and the top of the lower core part 326 and permits a resilient plantar flexion upon heel strike during the walking cycle. So as not to overstretch the damping cushion 328 during roll-over of the foot into the ball area during the walking cycle, a dorsal abutment 329 of the lower core part 326 engages over a shoulder 330 of the upper core part 325. The pivoting movement of the lower core part 326 with the ball area in the direction of the lower leg (dorsal flexion) is thus limited by the dorsal abutment 329.

In the fourth embodiment as shown in FIG. 11, the lower core part of the third embodiment together with the ball cushion is replaced by a flexion-elastic spring 431, which extends from the heel area to the toe area 424 of the artificial foot. The flexion-elastic spring 431 is shaped curving downward in the ball area, so as to thereby determine the ball-side contact surface 6.

In the heel area, the spring 431 serves to secure the heel cushion 421 on the underside, to hold the dorsal abutment 429 and also to mount the damping cushion 428 on the top of the spring 431.

The fifth embodiment as shown in FIG. 12 corresponds substantially to the fourth embodiment according to FIG. 9. However, the spring 531 extending along the length of the foot is not shaped as in FIG. 9 but instead extends substantially as a straight leaf spring into the toe area 524 of the foot. In the ball area, a ball cushion 522 is secured on the underside of the spring 531 in order to form the ball-side contact surface 6. In this embodiment, it is possible to adjust the rigidity in the toe area 524 by the leaf spring independently of the elasticity in the ball area, which is determined by the ball cushion 522.

In the sixth embodiment of a foot produced according to the invention, as shown in FIG. 13, the foot part 602 is composed exclusively of two shaped, flexion-elastic springs, namely a forefoot spring 632 and a heel spring 633. The lower leg connector part 604 is attached by an oblique surface to the correspondingly oblique connector surface 603. The oblique connector surface 603 is formed by the posterior end of the forefoot spring 632, in relation to which a correspondingly oblique and upwardly directed end of the heel spring 633 extends in parallel, wherein those portions of the forefoot spring 632 and of the heel spring 633 that extend in parallel are connected to each other. The virtual point of force introduction 605 is located centrally in the lower leg prosthesis part 604.

The forefoot spring 632 extends with a slight concave curvature from the connector surface 603 into the ball area and, with the curved design in the longitudinal direction in said ball area, determines the ball-side contact surface 6. From there, the forefoot spring 632 extends with an approximately rectilinear end into the toe area 624.

From the bearing surface 603, the heel spring 633 extends with a rearwardly directed curvature into the heel area and, with the corresponding curved design in the longitudinal direction in said heel area, forms the heel-side contact surface 7.

The spring hardness of the forefoot spring 632 and the spring hardness of the heel spring 633 are adapted to each other in such a way that the foot part 602 formed by the spring combination satisfies the condition according to the invention for the constant position of the center of gravity of the ground reaction forces.

The seventh embodiment of a foot produced according to the invention, as shown in FIG. 14, corresponds to the sixth embodiment shown in FIG. 11 but additionally has a sole spring 734 connecting the heel area of the heel spring 733 and the front part of the forefoot spring 732.

The sole spring is shaped in such a way that it adapts to the curved design of the heel spring 733 in the area of the heel-side contact surface 7 and to the curved design of the forefoot spring in the area of the ball-side contact surface 6. Between these, the sole spring 734 has a convex curvature in order to connect the contact surfaces 6, 7 like a bridge. The additional sole spring 734 ensures a more uniform distribution of the deformation energy to the forefoot spring 732 and the heel spring 733 upon loading during the walking cycle. Here too, the spring combination of the foot part 702 is adapted such that the constant position according to the invention of the resulting force vector of the ground reaction forces (body vector) is maintained.

The invention claimed is:

1. A method for producing an artificial foot which, in a longitudinal direction, has a medial plane in which a nominal foot length is defined as a distance from a heel to a foot tip of a natural foot replaced by the artificial foot, and which is designed with a top connector piece for the torsionally rigid connection of a foot insert extending substantially along the length of the foot, and which, seen along the length, bears on two contact surfaces of the artificial foot, of which a first heel-side contact surface is located in a heel area and a second ball-side contact surface is located in a ball area, and which is designed such that the top connector piece is connected to the contact surfaces of the foot part by spring connections, the method comprising:
   a) designing the contact surfaces to an approximately linear contact surface on a support,
   b) positioning a body vector as a resulting force vector of the ground reaction forces occurring on the contact surfaces in the rest state at a location along the artificial foot in a range between 40% and 48% of the nominal foot length, measured from the heel,
   c) loading the foot with weight loads between 25% of a lower nominal weight and 80% of an upper nominal weight from body weight along a coordinate arranged perpendicular to the support while in a standing position, and
   d) adapting the spring connections between the top connector piece and the contact surfaces in such a way that, during the loading according to step c), the body vector shifts by less than ±4% of the nominal foot length;
   wherein the foot insert contains a joint such that when the pivot point of the joint is placed in the body vector in the rest state of the artificial foot the joint, upon loading, permits an elastically damped rotation of the top connector piece relative to the heel-side contact surface without a change of length in a direction of gravity.

2. The method as claimed in claim 1, wherein the positioning of the body vector during the weight loads according to method step c) remains in a distance range between 42% and 46% of the nominal foot length.

3. The method as claimed in claim 1, wherein the foot insert is designed with a core and is connected to the contact surfaces via elastic pieces.

4. The method as claimed in claim 3 wherein the contact surfaces with the elastic pieces are determined from elastically compressible material.

5. The method as claimed in claim 4, wherein springs are used as elastic pieces.

6. The method as claimed in claim 1, wherein the foot insert is designed with a leaf spring which extends along the length of the foot insert and whose spring hardness decreases toward the toe area.

7. The method as claimed in claim 1, wherein a compressible spring is fitted between the heel-side contact surface and the top connector piece.

8. The method as claimed in claim 7, wherein the rotation movement is limited in the direction of expansion of the spring.

9. A method for producing an artificial foot, comprising:
   providing the artificial foot with a medial plane, a nominal foot length extending from a heel to a tip in a longitudinal direction, a top connector piece having a torsionally rigid connection to a foot insert which extends substantially along the length of the artificial foot, a heel-side contact surface located in a heel area, and a ball-side contact surface located in a ball area, the top connector piece being connected to the heel-side and ball-side contact surfaces with spring connections, the heel-side and ball-side contact surfaces defining approximately linear contact surfaces between the artificial foot and a support,
   positioning a body vector as a resulting force vector of ground reaction forces occurring on the contact surface in a rest state for the artificial foot in a range between 40% and 48% of the nominal foot length, measured from the heel;

loading the artificial foot with weight loads from body weight along a coordinate arranged perpendicular to the contact surface while in a standing position;

adapting the spring connections between the top connector piece and the heel-side and ball-side contact surfaces in such a way that, during the loading, the body vector shifts by less than ±4% of the nominal foot length;

wherein the foot insert contains a joint such that when the pivot point of the joint is placed in the body vector in the rest state of the artificial foot the joint, upon loading, permits an elastically damped rotation of the top connector piece relative to the heel-side contact surface without a change of length in a direction of gravity.

10. The method as claimed in claim 9, wherein the positioning of the body vector during the loading remains in a distance range between 42% and 46% of the nominal foot length.

11. The method as claimed in claim 9, wherein the foot insert is designed with a core and is connected to the heel-side and ball-side contact surfaces via elastic pieces.

12. The method as claimed in claim 11 wherein the heel-side and ball-side contact surfaces and the elastic pieces comprise elastically compressible material.

13. The method as claimed in claim 12, wherein the elastic pieces comprise springs.

14. The method as claimed in claim 9, wherein the foot insert includes a leaf spring which extends along the length of foot insert and whose spring hardness decreases toward the toe area.

15. The method as claimed in claim 9, wherein a compressible spring is fitted between the heel-side contact surface and the top connector piece.

16. The method as claimed in claim 15, wherein the rotation movement is limited in the direction of expansion of the compressible spring.

* * * * *